United States Patent
Van Der Vaart

[11] Patent Number: 5,849,973
[45] Date of Patent: Dec. 15, 1998

[54] OXIDATIVE COUPLING CATALYST

[75] Inventor: Donald R. Van Der Vaart, Raleigh, N.C.

[73] Assignee: Gas Research Institute, Chicago, Ill.

[21] Appl. No.: 786,495

[22] Filed: Jan. 21, 1997

Related U.S. Application Data

[60] Division of Ser. No. 541,455, Oct. 10, 1995, which is a continuation-in-part of Ser. No. 255,646, Jun. 8, 1994, abandoned, which is a division of Ser. No. 910,787, Jul. 8, 1992, Pat. No. 5,321,185.

[51] Int. Cl.[6] ............................................... C07C 2/02
[52] U.S. Cl. ................ 585/531; 502/258; 585/943; 585/700
[58] Field of Search ............. 423/328.2; 502/237, 502/258, 338; 585/531, 943, 500, 700

[56] References Cited

U.S. PATENT DOCUMENTS

| | | |
|---|---|---|
| 2,530,344 | 11/1950 | Watts . |
| 4,331,544 | 5/1982 | Takaya . |
| 4,427,578 | 1/1984 | Robinson et al. . |
| 4,444,984 | 4/1984 | Jones et al. . |
| 4,459,370 | 7/1984 | Van Der Wal et al. ............... 502/338 |
| 4,552,750 | 11/1985 | Van der Wal et al. . |
| 4,670,619 | 6/1987 | Withers, Jr. et al. . |
| 4,826,796 | 5/1989 | Erekson . |
| 4,886,931 | 12/1989 | Bartek . |
| 4,956,327 | 9/1990 | Erekson . |
| 4,957,718 | 9/1990 | Yoo . |
| 4,971,940 | 11/1990 | Kaminsky . |
| 5,024,984 | 6/1991 | Kaminsky . |
| 5,059,740 | 10/1991 | Kaminsky . |
| 5,068,215 | 11/1991 | Bartek . |
| 5,118,898 | 6/1992 | Tyler et al. . |

FOREIGN PATENT DOCUMENTS

| | | |
|---|---|---|
| 3503664 | 8/1986 | Germany . |
| 2148933 | 6/1985 | United Kingdom . |

*Primary Examiner*—Wayne Langel
*Assistant Examiner*—Tanaga Anne Boozer
*Attorney, Agent, or Firm*—Speckman Pauley Petersen & Fejer

[57] ABSTRACT

A catalyst for oxidative coupling of methane comprising $Fe_2O_3$ deposited on a silica substrate, said silica substrate having particle sizes in the range of about 150 to 215 μm, and a method for producing said catalyst in which particles of $Fe_2O_3$, with a particle size in the range from 100 to 150 μm, and particles of silica, with a particle size in the range from about 150 to about 215 μm are mixed together. The particles are heated to a temperature of at least about 800° C., after which the silica particles impregnated with $Fe_2O_3$ are separated from the remaining iron particles.

7 Claims, 9 Drawing Sheets

OXIDATIVE COUPLING CATALYST

This is a divisional application of co-pending U.S. patent application having Ser. No. 08/541,455, filed 10 Oct., 1995, pending, which application is a Continuation-in-Part of U.S. patent application Ser. No. 08/255,646, filed 8 Jun., 1994, now abandoned, which application is a divisional application of application Ser. No. 07/910,787, filed on 8 Jul., 1992, now issued as U.S. Pat. No. 5,321,185.

BACKGROUND OF THE INVENTION

1. Field of the Invention

This invention relates to a catalyst for the oxidative coupling of methane and a method for producing said catalyst.

2. Description of the Prior Art

In the search for petroleum, large amounts of natural gas are discovered in remote areas where there is no local market for it. The dominant technology now employed for utilizing remote natural gas involves its conversion to synthesis gas, a mixture of hydrogen and carbon monoxide. While syngas-based processes fulfill the need for an easily transportable liquid that can be converted to several useful products, synthesis gas is an expensive intermediate. Oxygen can be added with advantage to the rather inert methane molecule when products such as methanol or acetic acid are desired. In the case of hydrocarbons such as gasoline or diesel fuel, however, processes based on synthesis gas essentially require the addition of oxygen, followed by its removal, increasing final product cost.

Methane, the predominant component of natural gas, although difficult to activate, can be reacted with oxygen or oxygen-containing compounds such as water or carbon dioxide to produce synthesis gas in a process known generally as reforming. This mixture can be converted to higher hydrocarbons using, for example, Fischer-Tropsch technology, and then upgraded to transportation fuels using usual refining methods. Alternatively, the mixture can be converted to liquid oxygenates which in turn can be converted to more conventional transportation fuels by catalysts such as certain zeolites.

Because reforming requires high capital investment and energy inefficient processing (as in steam reforming, where fuel is burned to supply heat of reforming) and represents an indirect route to the production of hydrocarbons, other means of converting methane directly to higher hydrocarbons are needed.

Oxidative coupling has been recognized as a promising approach to the problem of methane conversion although its mechanism is not completely understood. In such processes, methane is contacted with solid materials referred to by various terms including catalysts, promoted-catalysts, activators, conversion catalysts, or upgrading catalysts. Methane mixed with oxygen and allowed to contact the catalyst is directly converted to ethane, ethylene, higher hydrocarbons and water. The conversion of methane to carbon dioxide, which is, in essence, the highly favored thermodynamical process of combustion, is undesirable as both oxygen and carbon are consumed without producing the desired higher value $C_{2+}$ hydrocarbons. In order to avoid complete combustion, many methods for oxidative conversion have been carried out in the absence of an oxygen-containing gas, relying on the oxygen supplied by an oxide catalyst itself. Such catalysts can then be regenerated (off cycle) by re-oxidation.

Catalytic mixtures of yttrium-barium-copper oxides are highly active and 100% selective for producing $CO_2$, that is, they are combustion catalysts. In order to obtain the required selectivity to hydrocarbon formation, Group IA metals, particularly lithium and sodium, have been used in such catalytic mixtures. Under the conditions used for oxidative coupling, however, migration and loss of the alkali metal normally occurs. Thus, there is a need for highly active, $C_{2+}$ hydrocarbon-selective and stable oxidative coupling catalysts, and new or improved processes for these.

A three-component catalyst for the oxidative conversion of methane to hydrocarbons containing two or more carbon atoms is disclosed in U.S. Pat. Nos. 5,024,984 and 5,059,740 to Kaminsky et al. Improvements in methanation reaction are disclosed in U.S. Pat. No. 4,331,544 to Takaya et al. A process for the removal of sulfur oxides from a gas is disclosed in U.S. Pat. No. 4,957,718 to Yoo et al. A number of patents describe methane oxidative coupling, such as U.S. Pat. Nos. 4,956,327 and 4,826,796 to Erekson et al, U.S. Pat. No. 4,971,940 to Kaminsky et al., and U.S. Pat. Nos. 5,068,215 and 4,886,931 to Bartek et al. Catalyst conversion is also discussed in "The Conversion of Methane to Ethylene and Ethane with Near Total Selectivity by Low Temperature (<610° C.) Oxydehydrogenation over a Calcium-Nickel-Potassium Oxide Catalyst", *J. C. Baltzer A. G. Scientific Publishing Company*, page 225–262, P. Pereira, S. H. Lee, G. A. Somorjai and Heinz Heinemann, July 1990, and "New Cost Effective Methane Conversion Process," *Technology Announcement*, Lawrence Berkeley Laboratory. A process in which no carbon oxides are produced at all, however, offers some disadvantages in the context of processes located at remote well sites. In particular, heat would need to be generated outside of the process unit and transferred to the reactor. This is generally an inefficient process.

A fluidized bed offers a unique chemical environment for gas-solid reactions by providing efficient contact between the gas and the solid phases while offering excellent rates of heat dissipation. For these reasons, the fluidized-bed reactor is the reactor configuration of choice for many exothermic reactions, including catalytic oxidations such as the partial oxidation of naphthalene to produce phthalic anhydride, and noncatalytic oxidation reactions, such as coal combustion. Despite this history, however, very little work has been reported on the use of a fluidized bed for methane oxidative coupling (MOC).

Much of the research on MOC has focused on the identification of more active and/or more selective catalyst formulations in an effort to improve the overall yield of higher hydrocarbons. Virtually all of this work has involved the use of fixed-bed microreactors for testing while the metal oxides under investigation have been quite exotic or expensive. Clearly, a considerable materials-development effort would be required to prepare an attrition-resistant catalyst from any of these formulations which would be suitable for fluidized bed applications.

MOC has received considerable attention in recent years, initiated, in large part, by the work of G. E. Keller and M. M. Bhasin, "Synthesis of Ethylene via Oxidative Coupling of Methane," *Journal of Catalysis* 73, 9–19 (1982) and John A. Sofranko, John J. Leonard and C. Andrew Jones, "The Oxidative Conversion of Methane to Higher Hydrocarbons," *Journal of Catalysis* 103, 302–310, (1987). These works focused on screening many different metal oxide catalysts on the basis of ethane/ethylene ($C_{2,total}$) yield according to the reaction,

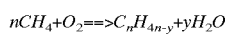

Work since that time has generally centered on metals identified in these studies, although more exotic metals or mixtures of these have been considered. Most work has been in fixed-bed microreactors despite the fact that a fluidized-bed reactor would likely be the preferred commercial reactor.

SUMMARY OF THE INVENTION

It is an object of this invention to provide a catalyst for use in the oxidative coupling of methane to produce higher hydrocarbons.

It is an object of this invention to provide a catalyst for oxidative coupling of methane which is highly active and $C_{2+}$ hydrocarbon-selective.

These and other object of this invention are achieved by a catalyst composition comprising $Fe_2O_3$ deposited on a silica substrate, said silica substrate having a geometric surface of about 0.04 $m^2/g$.

It has been found that, contrary to prior disclosures by Keller and Bhasin (1982), iron oxide is advantageous as a MOC catalyst. The work was performed on the heterogeneous and homogeneous reactions of methane in a 7.0 cm I.D., all-ceramic fluidized-bed reactor. The instant disclosure also shows that the addition of water to the reactant mixture enhances the selectivity of the process.

The instant invention discloses a very inexpensive material for use as an active methane oxidative coupling catalyst. The catalyst material in accordance with this invention, when prepared for MOC catalysis in accordance with the method disclosed herein, is extremely resistant to attrition. These are two of the requirements for a practical, commercially useful, fluidized bed catalyst.

BRIEF DESCRIPTION OF THE DRAWINGS

These and other objects and advantages of this invention will become apparent when the specification is read in conjunction with the drawings wherein.

DESCRIPTION OF PREFERRED EMBODIMENTS

Figure 1:
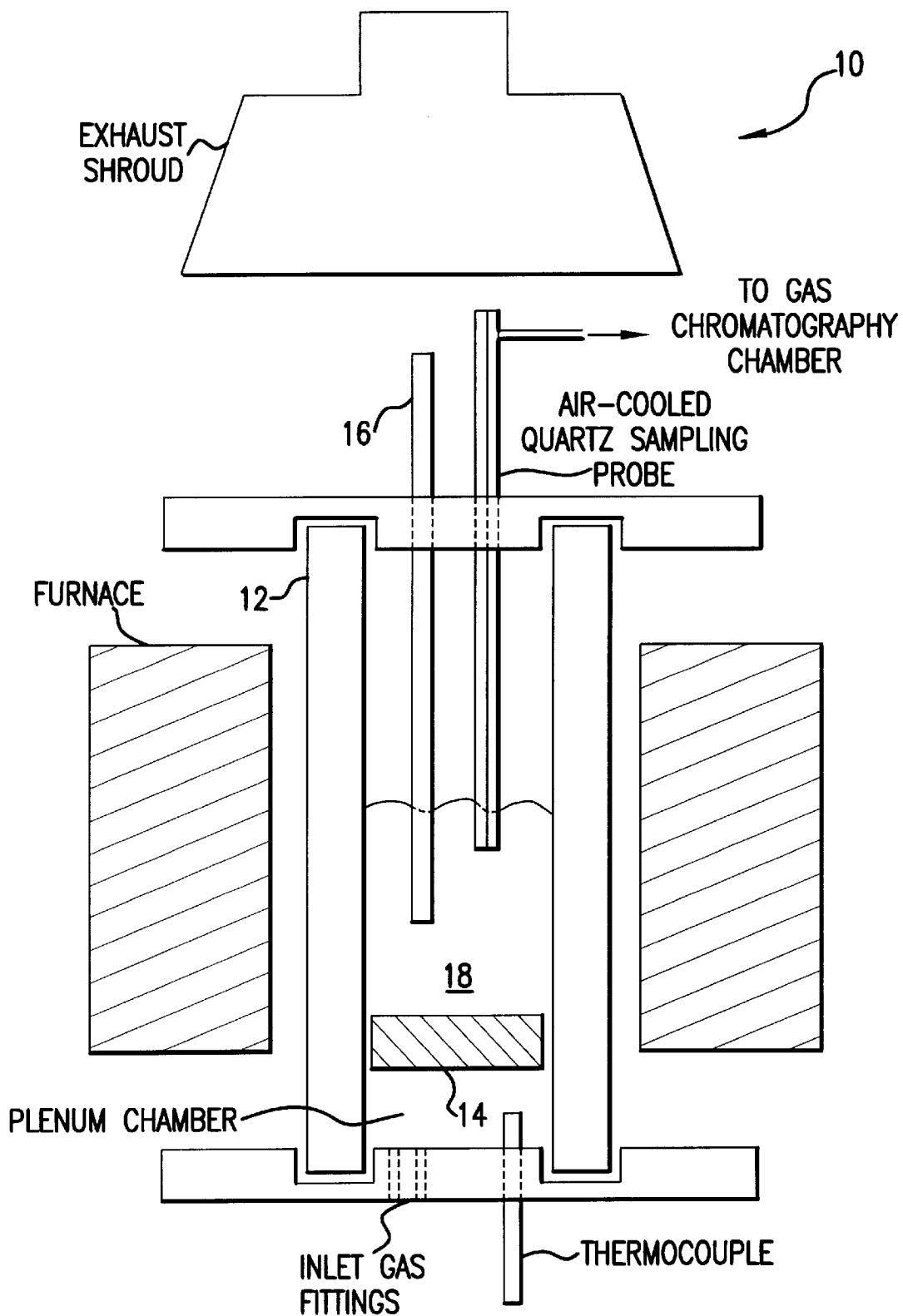
FIG. 1 is a schematic of the reaction of the instant invention.

In FIG. 1, the fluidized-bed reactor used in the examples herein is described. All-ceramic materials were used in reactor construction to limit undesired catalytic effects. The example reactor 10 was a ceramic tube 12, 7.0 cm ID, (99.8% $Al_2O_3$) fitted with a 1 cm thick, 7 cm O.D. porous alumina disk as a distributor 14. The alumina disk 14 is of the type fabricated by the Selee Corporation. The disk was cemented inside the tube using a high temperature cement, such as Sauereisen Awseal Adhesive cement, No. 2 paste. The top of the distributor 14 is placed to be just above the bottom of the heating coils of the furnace. A ceramic sheathed type-K thermocouple 16 was placed in the bed 18 approximately 4 cm above the distributor 14. A complete description of the apparatus is given in *Industry and Engineering Chemistry Research*, Vol. 31, No. 4, pages 999–1007, Donald Van der Vaart (1992), which is incorporated herein by reference.

The steam required for these tests was produced through heating 3-times distilled, deionized liquid water to approximately 170° C. and pumping it through a ⅛" OD stainless steel vaporizer coil. The mixture was then mixed with the $CH_4/N_2/O_2$ mixture. A pressure regulator was placed upstream of the mixing "tee" to provide a uniform flow.

Gas samples were drawn from various points along the axial direction and at the midway point between the wall and the centerline in the radial coordinate. An air-cooled quartz probe enabled sampling both in and over the fluidized bed. A gas chromatograph, such as the Hewlett-Packard model 5890 series II, was equipped with a HP 3396A electronic integrator and employed a two-column switching technique to analyze for $CH_4$, CO, $CO_2$, $H_2$, $N_2$, $O_2$, $C_2H_4$ and $C_2H_6$. The carbon balance (mass of carbon atoms in input—mass of carbon atoms in output) for all the results presented herein was within ±5% of the mass of carbon atoms in input.

The gas samples are taken periodically by a sampling probe immersed in a fluidized-bed reactor. The sample provides an average of the gas in the bubble/cloud phase and the gas in the emulsion phase. Because the extent of reaction in these two phase is, in general, different, the concentration sampled by the probe depends on the proportion of each phase drawn. This has been described in detail in *AICHE Journal*, 1992, and is incorporated herein by reference.

A physical mixture of pure $Fe_2O_3$, having a particle size of approximately 100–150 μm and high purity silica sand, having a particle size of approximately 150–215 μm, was fluidized under high temperature conditions. The temperatures ranged from 800° C. to 950° C. in both reducing and oxidizing atmospheres. The iron tended to agglomerate to form larger iron "clinkers" which subsequently fell to the bottom of the reactor. These clinkers further agglomerated at the bottom to form larger masses of iron. During this process, some of the iron distributed itself on the surface of the silica sand. The iron impregnated silica sand was separated from both the agglomerated iron and the remaining iron particles. This material was then used in the MOC tests described herein.

SEM photographs show that the instant catalytic material is non-porous with an extremely small surface area, average geometrical surface area being 0.04 m²/g. An ESCA surface analysis measured the surface concentration of Fe on the catalyst to be 2 wt. %. Untreated sand has a Fe concentration of approximately 0.9 wt %. To establish the role of homogeneous reactions, a sample of this untreated sand was repeatedly washed with 0.5N hydrochloric acid to dissolve the iron and/or iron oxide(s) present, yielding a surface concentration of 0.6 wt % Fe. The washed sand is used as a baseline and referred to hereinafter as purified sand. The foregoing material is used in the following MOC examples and the manufacture of this material has been shown to be reproducible.

EXAMPLE I

A bed with a height at minimum fluidizing velocity ($H_{mf}$) of 7.7 cm was fluidized by a mixture of 5% methane and 3% oxygen in 92% nitrogen. The reactor temperature was varied from 750° C. to 900° C. The excess fluidizing velocity was kept constant at 20 cm/sec, which was evaluated at the reactor temperature.

EXAMPLE II

A bed with a height at minimum fluidizing velocity ($H_{mf}$) of 7.7 cm was fluidized by a mixture of 5% methane and 3% oxygen in 87% nitrogen and 5% water. The reactor temperature was varied from 750° C. to 900° C.

Figure 2:
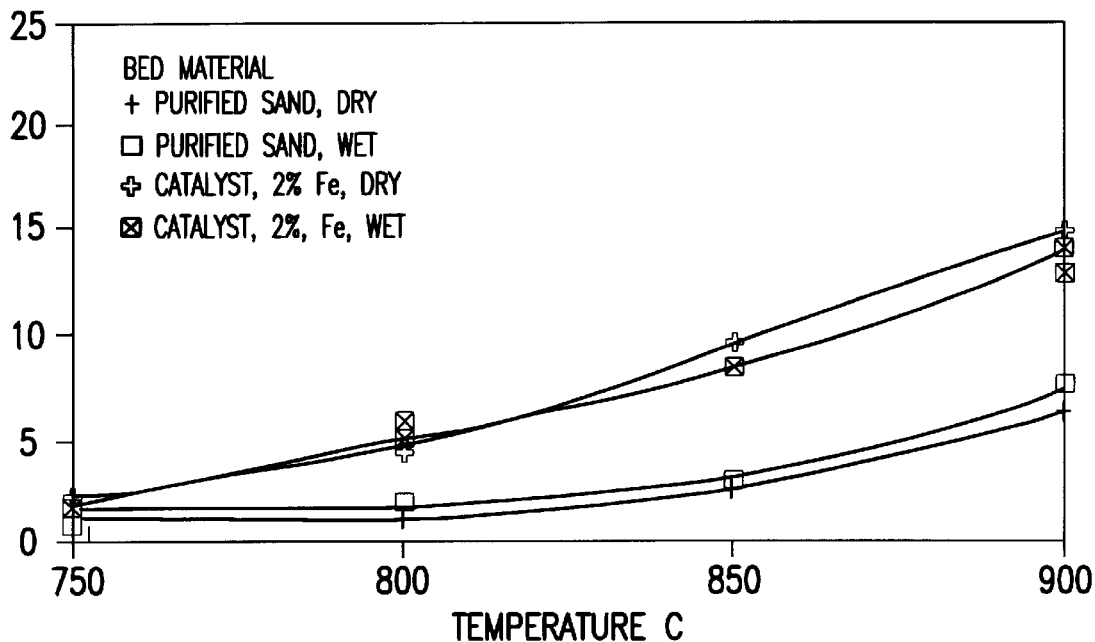
FIG. 2 is a chart of fractional conversion as a function of temperature.
Figure 3:
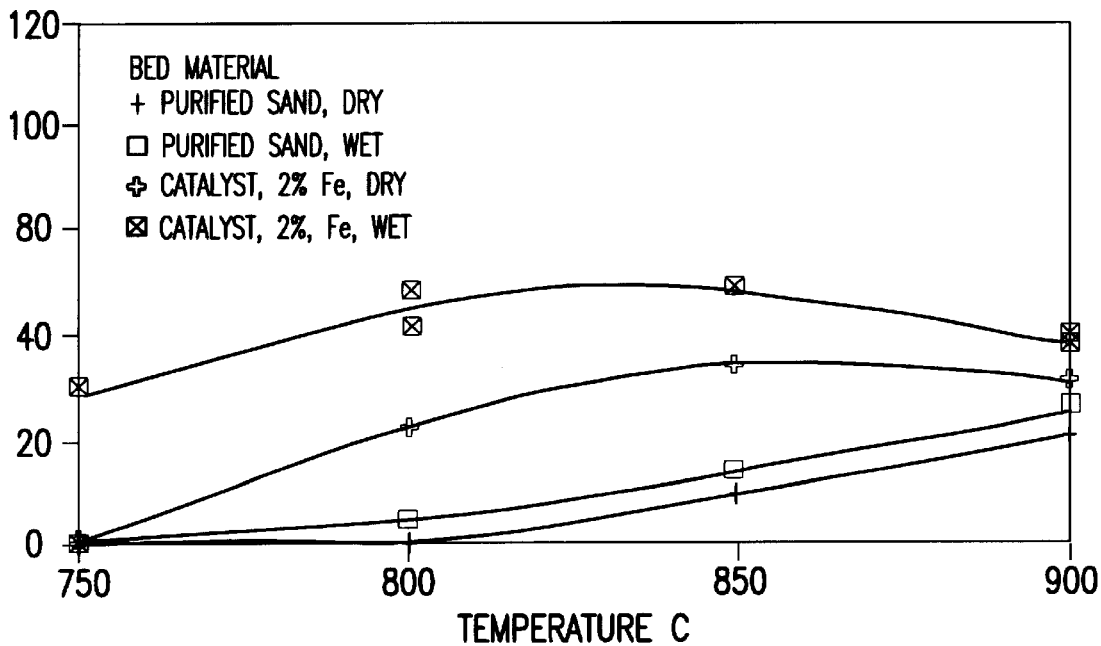
FIG. 3 is a chart of selectivity to total $C_2$ as a function of temperature.
Figure 4:
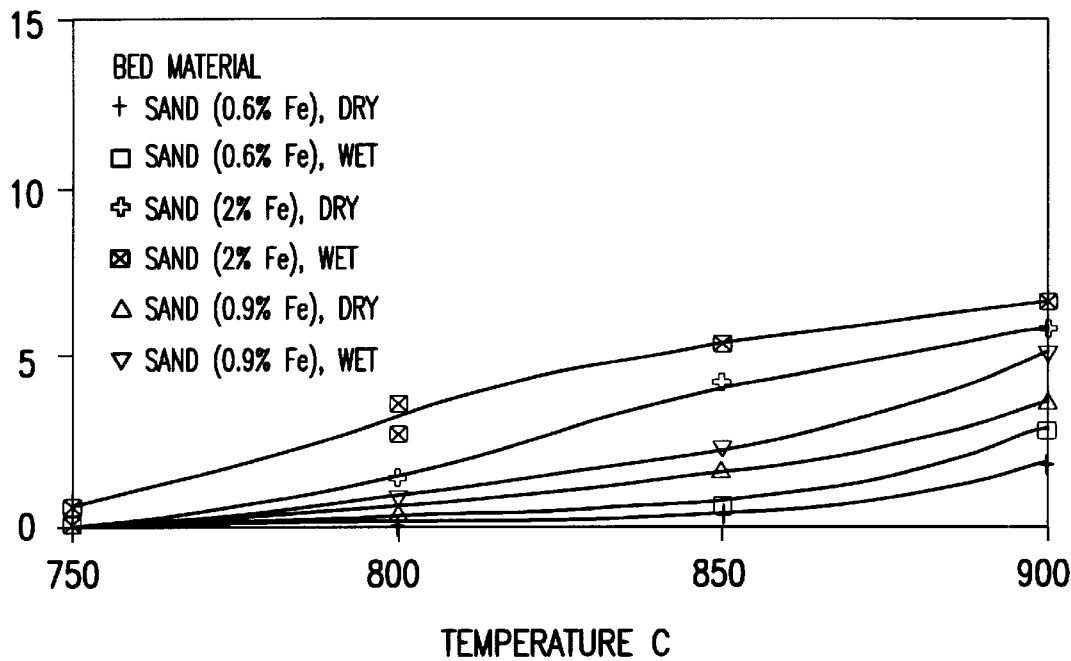
FIG. 4 is a chart of the yield of total $C_2$ as a function of temperature.

FIGS. 2 and 3 compare the reactivity and $C_2$ selectivity for MOC of the purified sand and the $Fe_2O_3/SiO_2$ material as a function of temperature. The $C_{2,t}$ yields using the Fe catalyst, unpurified sand and the purified sand are illustrated in FIG. 4. The yield increases as the percentage of Fe on the sand increases. The addition of water suppresses the $CO_2$ formation and, to a lesser extent, CO. The presence of a small amount of iron on the purified sand is consistent with the effect of the water being surface related. Fe sites are responsible for $CO_x$ formation and $H_2O$ adsorbs on some of these sites, thereby inhibiting $CO_x$ formation. Fewer Fe sites implies less of an effect by $H_2O$.

Figure 5:
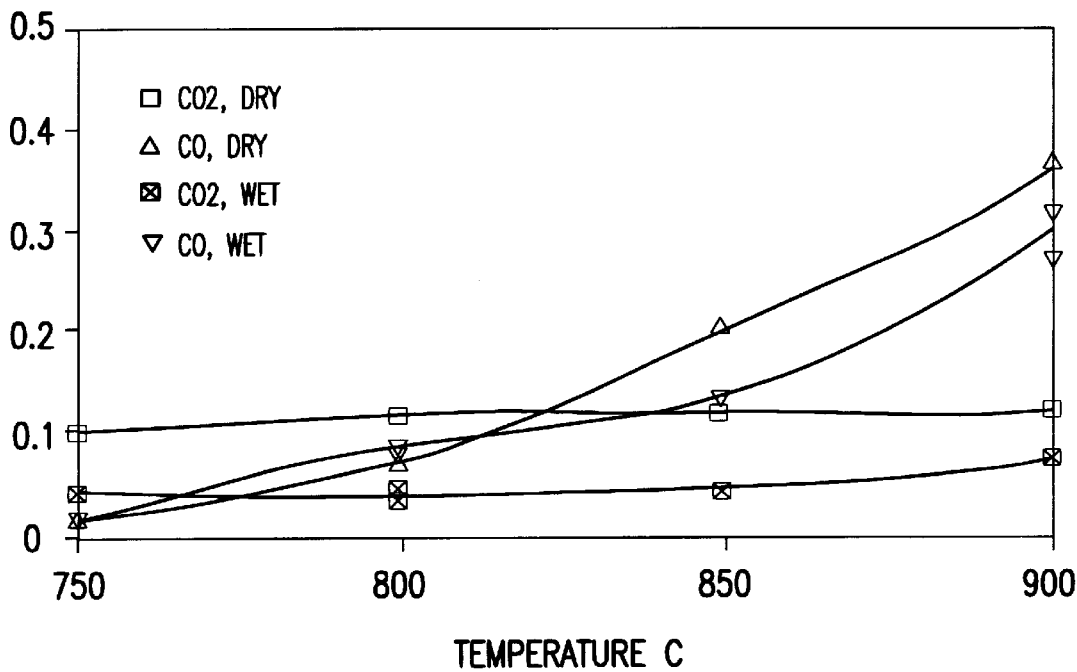
FIG. 5 is a chart of the concentration of carbon oxides as a function of temperature.

FIG. 5 illustrates the distribution of carbon oxides for two different conditions. The MOC catalyst is shown tested both with and without water.

The in-bed probe concentration is given by the equation:

$$C_{probe} = \frac{U_{br}}{U_{abs}} C_e + \frac{U - U_{mf}}{U_{abs}} C_b \quad (2)$$

where U is the superficial fluidizing velocity, $U_{mf}$ is the minimum fluidizing velocity and the subscripts e and b refer to the emulsion- and bubble-phases, respectively. The relative bubble rise velocity, $U_{br}$, is given by Davidson and Harrison (1963) as, $$(3) \quad U_{br} = 0.711 \sqrt{gD_b}$$

where g is the gravitational constant and $D_b$ is the bubble size. The absolute rise velocity, $U_{abs}$, is given as, ibid, $$(4) \quad U_{abs} = U - U_{mf} + U_{br}$$

For a typical bubbling bed of group B particles, equation (2) predicts that the sampled gas is composed of approximately an equal amount of bubble- and emulsion-phase gas. This is a much larger proportion of emulsion-phase gas than would be expected if the probe drew a volumetric mixture which is given as, $$C_{probe} = \frac{U_{mf}}{U} C_e + \frac{U - U_{mf}}{U} C_b \quad (5)$$

Thus, in the case of a catalytic reaction for which the conversion is higher in the emulsion-phase, a shift in an average from one more heavily weighted towards the emulsion-phase (i.e., $C_{probe}$ in the bed) to one weighted more towards the bubble phase (i.e. $C_{probe}$ in the freeboard) would exhibit a decrease in conversion. This point is illustrated below. It should be pointed out that the freeboard concentration is the same as the reactor effluent concentration and is given by equation (5). In presenting the data, the following definitions were used: the selectivity, φ, was defined by Sofranko et al (1987) as, $$\phi = \frac{2 \times C_{-2,t}}{\text{mole CH}_4 \text{ converted}} \quad (6)$$

where $C_{2,t}$ represents the total concentration of $C_2$ hydrocarbons (i.e., ethane and ethylene). The "2" is the stoichiometric coefficient, n, in reaction (1). The product yield, φ, is defined as the product of φ and the methane conversion or, $$\Phi = \frac{2 \times C_{-2,t}}{\text{mole CH}_4 \text{ fed}} \quad (7)$$

Figure 6:
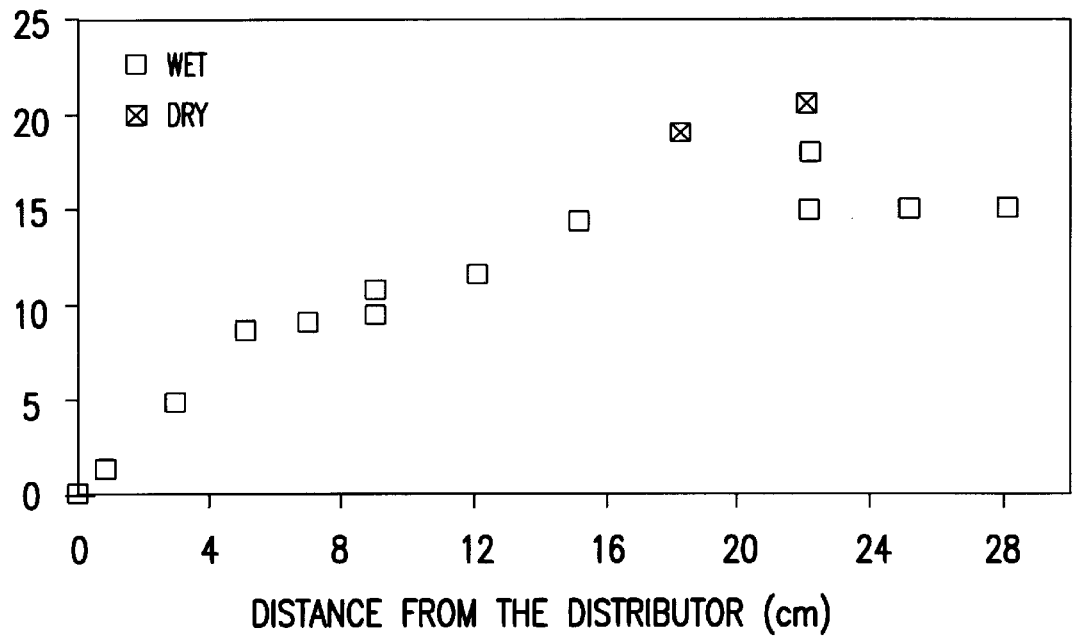
FIG. 6 is a chart of the fractional conversion profile for methane oxidative coupling.
Figure 7:
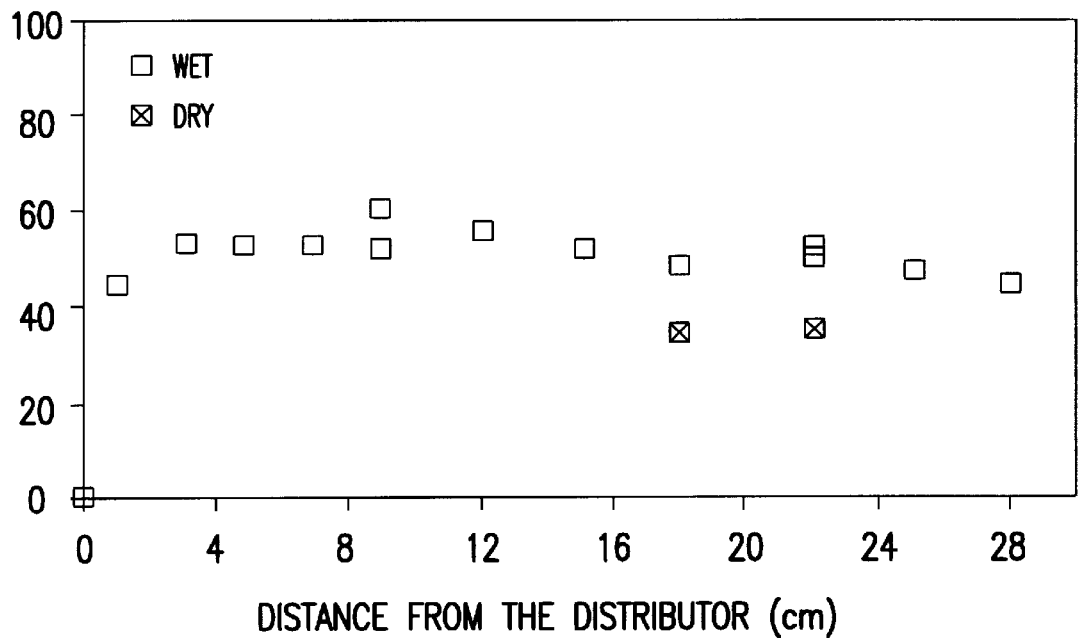
FIG. 7 is a chart of the selectivity for total $C_2$ for methane oxidative coupling.

The conversion and selectivity profiles of FIGS. 6 and 7 illustrate the complexity introduced by the fluidized bed reactor. The reactor was greater than 15 cm deep (slumped bed height) with an expanded bed height of approximately 20 cm for an excess fluidizing velocity of 10 cm/s. The influence of the added water is more pronounced at this bed height. The maximum in the fractional conversion is not an experimental anomaly, but due rather to the differences in the probe concentrations for gas sampled at different points within the reactor (i.e. within the bed vs. over the bed). The in-bed probe concentration is given by equation (2). Over the bed (i.e., in the freeboard), however, the gas mixes according to the volumetric average of the two phases (equation (5)).

Figure 8:
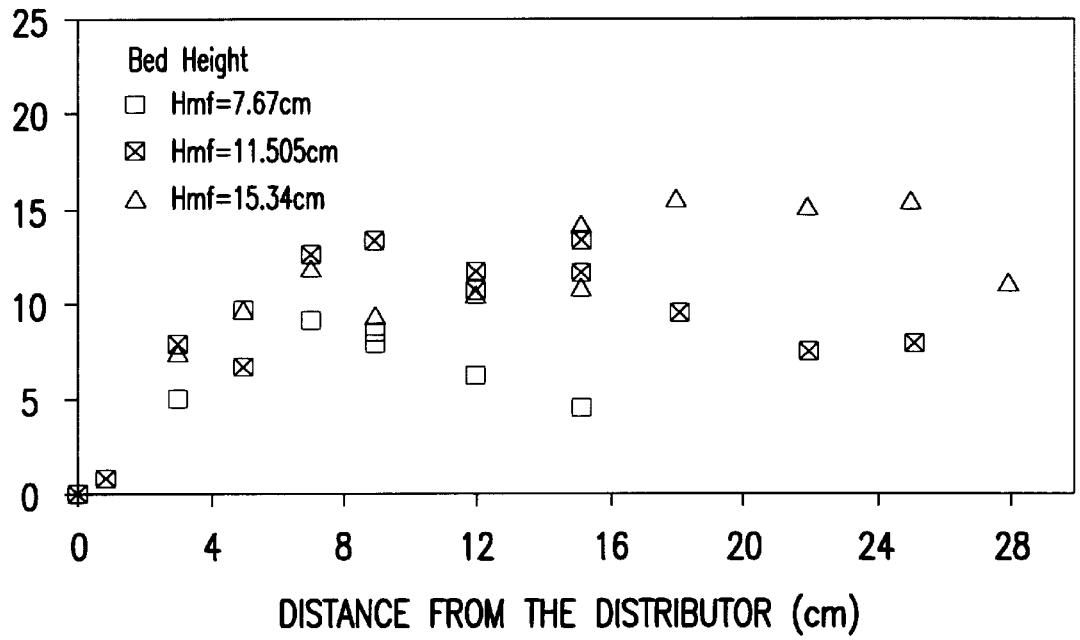
FIG. 8 is a chart of the fractional conversion profile for methane oxidative coupling.
Figure 9:
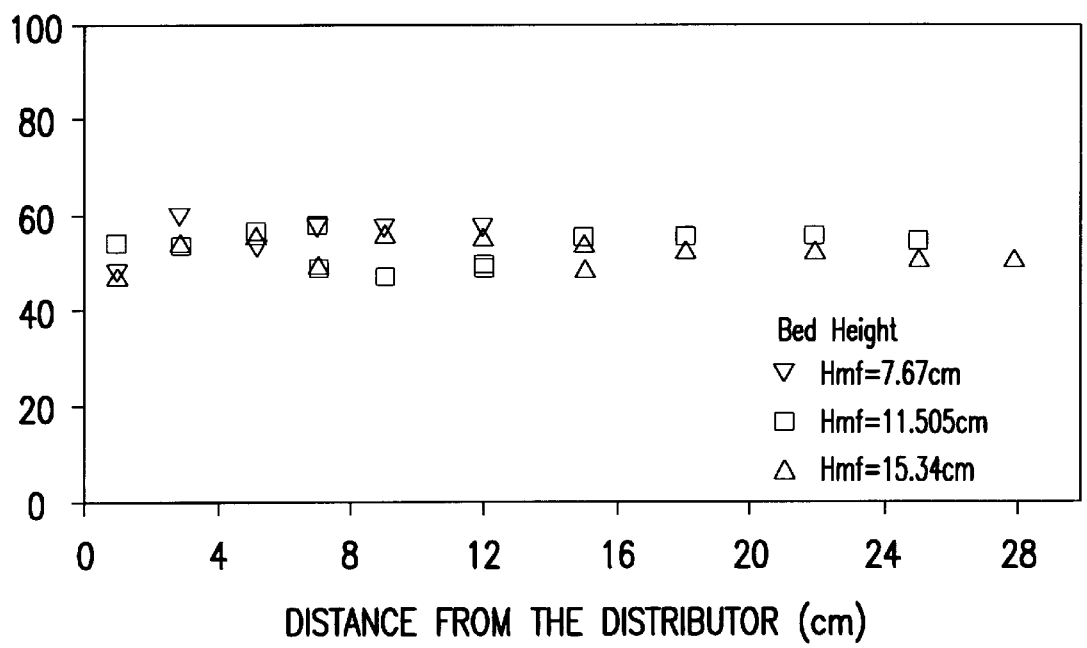
FIG. 9 is a chart of the selectivity profile of total $C_2$ as a function of bed height.

FIGS. 8 and 9 illustrate the effect of bed height on the MOC reactions. The increase in the bed height leads to an increase in the residence time of the gas in both the bubble- and emulsion-phases. Since the bubbles grow as they rise through the bed and their rise velocity increases as they grow, the increase in their residence time is not linearly proportional to the bed height. At this excess fluidizing velocity, slugging was observed for the deepest bed ($H_{mf}$= 15.3 cm). Consequently, the increase in the conversion of methane is more evident in the 11.5 cm bed than in the 15.3 cm bed. The maximum in the conversion profile caused by the sampling probe-effect is seen in each of the three bed heights.

The bed height had very little effect on the selectivity for $C_{2,total}$. Since the fractional conversion increased with bed height, substantial gains in the $C_{2,t}$ yield can be realized if the bed height is increased as long as slugging can be avoided. This is illustrated in Example III for lower-excess fluidizing velocity.

Figure 10:
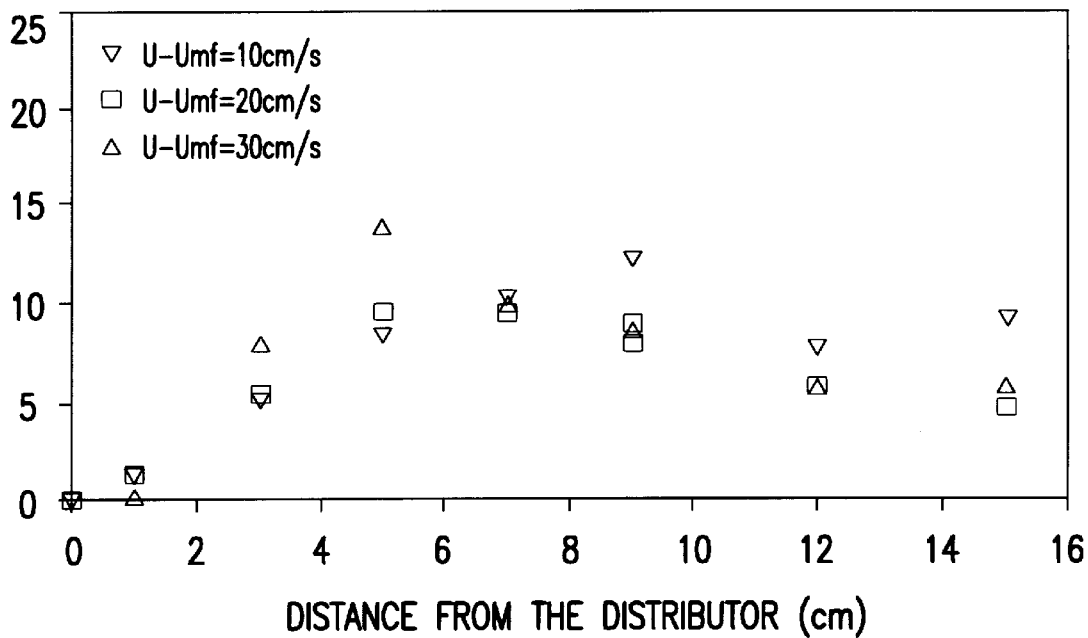
FIG. 10 is a chart of fractional conversion profile for methane oxidative coupling.
Figure 11:
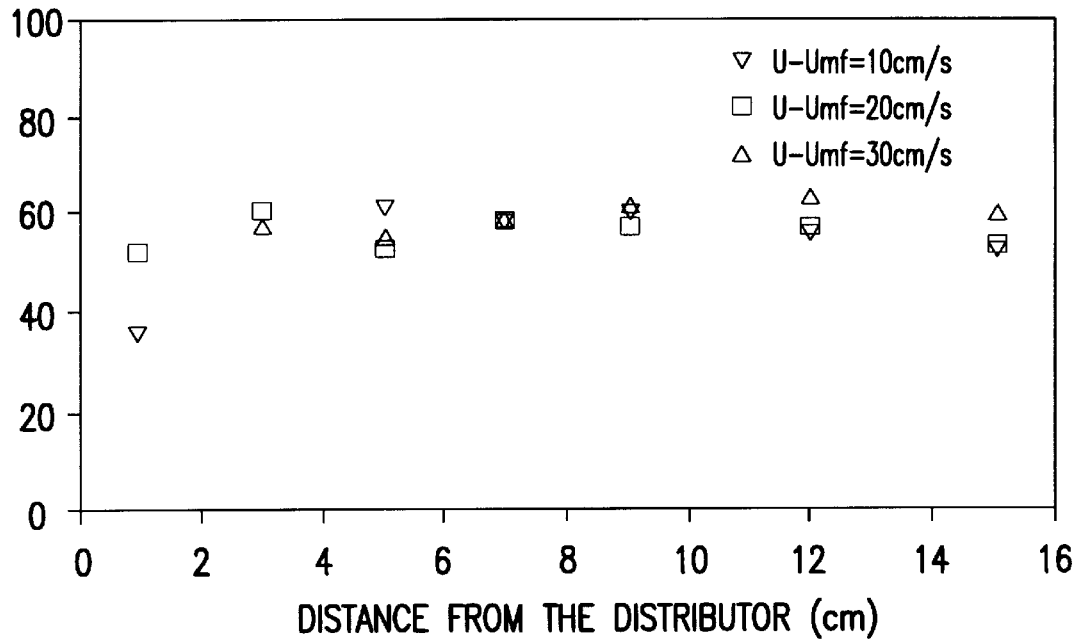
FIG. 11 is a chart of selectivity profile for methane oxidative coupling.

The effect of the excess fluidizing velocity is shown in FIGS. 10 and 11. Increasing the excess fluidizing velocity effects the performance of the fluidized reactor in a number of ways: i) the two-phase theory predicts that the increased gas flow only increases the flow in the bubble phase. That is, the gas flow rate through the emulsion phase is not increased. This leads to larger bubbles and reduces the residence time of the gas in the bubble-phase. ii) The more violent solids-mixing induces more gas back-mixing in the emulsion phase, and iii) the expanded bed height is increased which changes the length of the splash zone, where the volumetric fraction of solids is intermediate between the dense bed and the freeboard.

Figure 12:
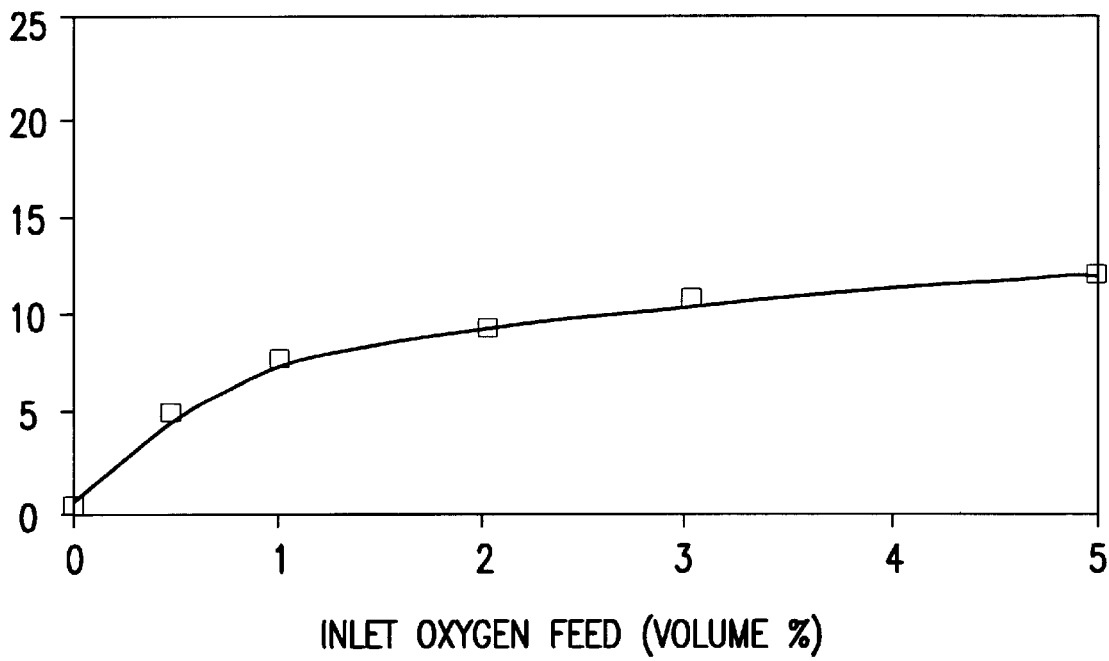
FIG. 12 is a chart of fractional conversion as a function of oxygen concentration.
Figure 13:
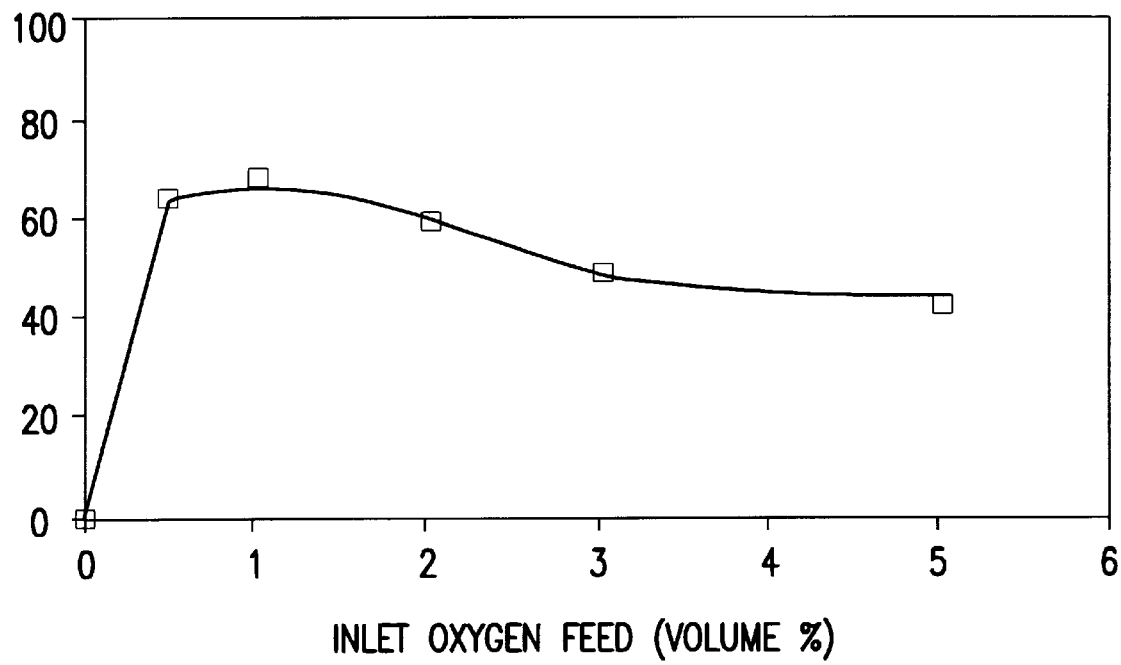
FIG. 13 is a chart of selectivity as a function of oxygen concentration.

The effect of changes in the inlet oxygen concentration are illustrated in FIGS. 12 and 13. The conversion of methane increases as the oxygen concentration is increased. The selectivity passes through a maximum at an oxygen concentration of about 1%.

Figure 14:
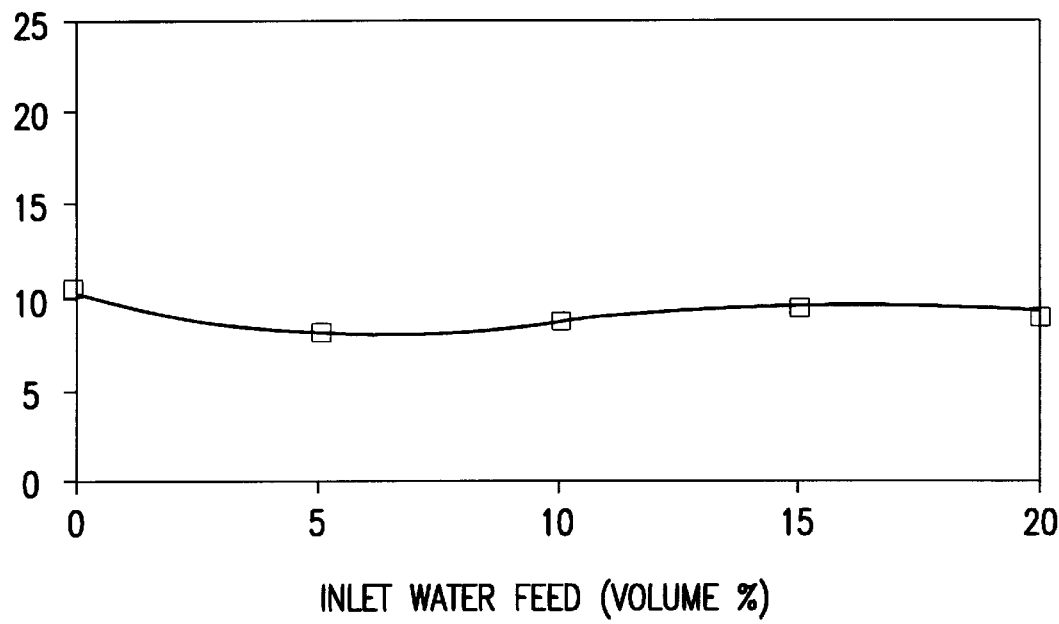
FIG. 14 is a chart of fractional conversion as a function of inlet water concentration.
Figure 15:
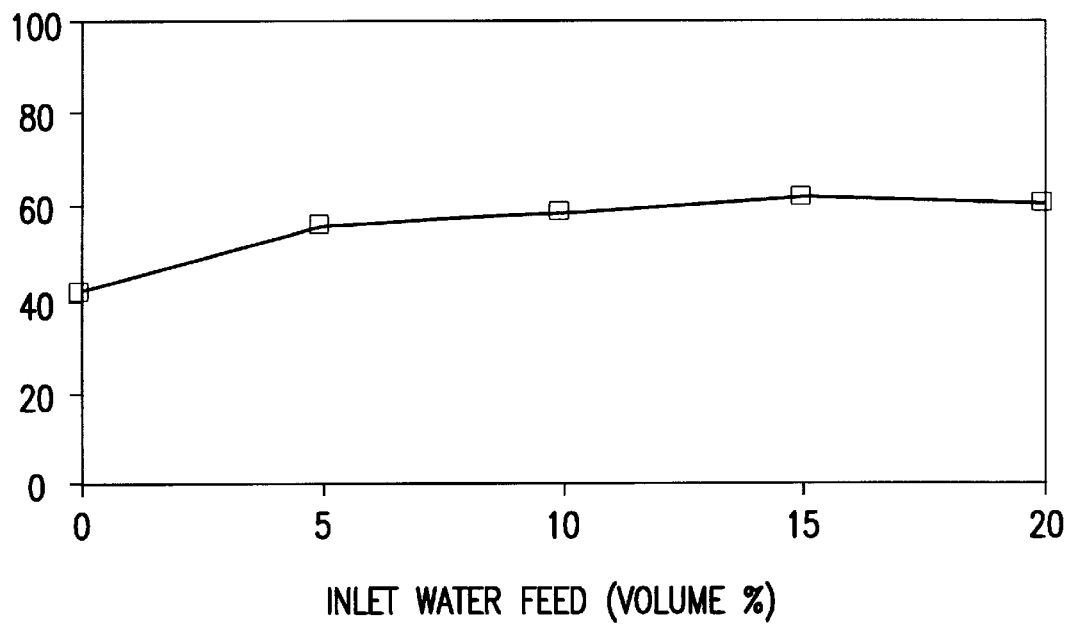
FIG. 15 is a chart of selectivity of total $C_2$ as a function of inlet water concentration.

The effect of steam on the MOC reactions is shown in FIGS. 14 and 15. A slight trade-off is seen between conversion and $C_{2,t}$ selectivity at low water conversions. The added water is more manifest for deeper beds, as illustrated in Example III.

Figure 16:
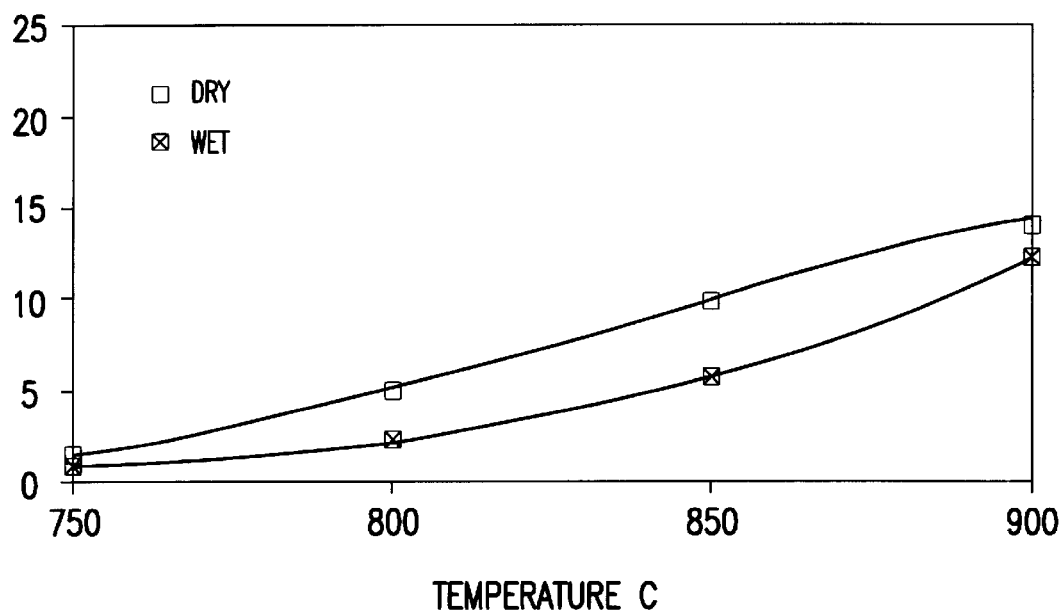
FIG. 16 is a chart of fractional conversion profile for methane oxidative coupling.
Figure 17:
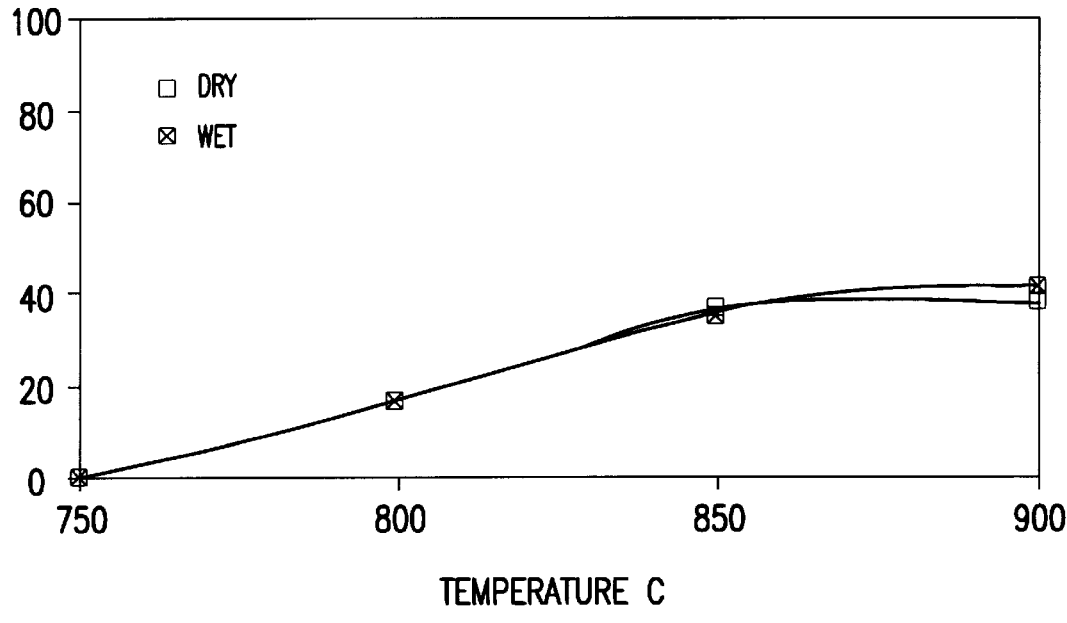
FIG. 17 is a chart of selectivity profile of total C2 for methane oxidative coupling.

A series of tests were performed using pure α alumina particles ranging in diameter from 0.15 to 0.21 mm. This material was shown by SEM to be porous and therefore contained more surface area than the $SiO_2$ sand used in previous examples. The surface of this material was void of any Fe, as indicated by ESCA testing. The fractional conversion and selectivity for this material are illustrated in FIGS. 16 and 17. Different chemistry is involved over this material, presumably indicative of the more acid character of alumina relative to $SiO_2$. Comparison of FIGS. 16 and 17 with FIGS. 2–4 show that the fluidized bed is not solely responsible for the success of the $Fe_2O_3/SiO_2$ catalyst.

Contrary to previous conclusions, the instant material is viable as a catalyst for MOC. The differences in the formulation and the reactor/catalyst system used in previous studies, by Keller and Bhasin, and in the instant disclosure lead to a dramatic difference in the performance of $Fe_2O_3$ as a methane oxidative coupling catalyst. These differences are discussed herein in the context of the tentative reaction mechanism put forth in the literature.

From the view that MOC is a heterogeneously catalyzed gas phase reaction, prior research put forth a schematic representation of the "possible reaction pathways" for MOC. This scheme provided for parallel gas-phase and surface-catalyzed partial oxidation reactions with continuous interaction between the phases. The only significant difference in the two reaction pathways was that hydrocarbon coupling reactions were assumed to occur only in the gas-phase. Thus, surface involvement is assumed to be undesirable beyond initial activation of the $CH_3$—H bond. The implication is that an upper limit can exist on the specific surface area of a successful MOC catalyst and that this limit depends on the metal oxide(s) used. In comparison to the iron oxide catalyst tested by Bhasin and Keller (1982), the surface area of the $Fe_2O_3$— coated sand used in this study was more than two orders of magnitude smaller.

An additional advantage of the catalyst formed in the present study over that used by Bhasin and Keller (1982) could be the catalyst support. Jones et al. (1987) reported an improvement in MOC selectivity when using a silica support versus α—$Al_2O_3$ (the latter was used by Bhasin and Keller). The poor performance of the pure α—$Al_2O_3$ reported here is consistent with this observation.

Thermal effects could also improve the MOC performance of the fluidized-bed vis-a-vis a packed-bed. Specifically, if MOC does proceed via a hetero-homogeneous mechanism in which the methyl radicals are formed on the solid surface, it is likely that much of the heat release would occur in the gas phase due to radical recombination reactions there (see Law 1988). It may be expected, then, that significant thermal gradients could exist between the solid and gas phases which would affect product selectivity. This gradient would be more pronounced in the plug-flow reactor with its one-dimensional flow profile than in a fluidized bed in which the random movement of the solids continuously disrupts the development of a temperature maximum.

While this disclosure emphasizes $Fe_2O_3$, other metal oxides would, when deposited on similarly low surface area supports, exhibit similarly improved performance. This includes other metal oxides that were previously reported by Keller & Bhasin to be inactive for $C_2$ formation or overly active for complete oxidation, including Ni, Cu, Zn and Ag. Silica is a unique support or substrate, in that it is attrition-resistant and, therefore, advantageous for use in a fluidized-bed.

The instant invention shows that the addition of water improves the selectivity of the catalytic MOC reactions. Water occupies catalytic sites on the catalyst which would otherwise serve to oxidize the methyl radicals before they desorb, thereby preferentially "poisoning" the catalyst. Similarly, water can successfully compete with, for example, $C_2$ species formed in the gas-phase and thereby limit their subsequent adsorption and oxidation. A surface-inhibition mechanism by water is further supported by the asymtotic dependence of selectivity on water concentration as shown in FIG. 15. This implies a limit on surface sites on which water can adsorb.

Roos et al. (1990) support the theory that $CO_2$ is formed primarily on the catalyst surface while CO is formed via gas-phase reactions. This would indicate that two sites are present on the surface of the $Fe_2O_3/SiO_2$ catalyst: i) a site not poisoned by water which catalyzes the formation of the methyl radical, and ii) a site that is poisoned by water which promotes $CO_2$ formation regardless of the precursor. The distribution of $CO_2$ shown in FIG. 5 supports this mechanism.

The unique environment of the fluidized bed also contributes to the production of $C_{2,t}$. The majority of the MOC reactions take place in the emulsion-phase, making the fluidized bed reactor somewhat similar to a cyclic oxygen-feed (Redox-feed) system despite the fact that both oxygen and methane are co-fed to the reactor. This is because the emulsion-phase gas is flowing in a plug (more or less depending on the excess fluidizing velocity) so that the gas-phase oxygen concentration will be depleted rather quickly there. The catalyst, on the other hand, is continually mixed throughout the reactor and, therefore, comes in contact with oxygen which is comparatively plentiful in the bubble-phase (where little reaction is occurring). Gaseous oxygen, as opposed to catalyst-bound oxygen, is also transferred between the two phases throughout the reactor. Thus oxygen is supplied to the emulsion-phase gas in a distributed fashion which was indicated by Jesus M. Santamaria, Eduardo E. Miro and Eduardo E. Wolf, "Reactor Simulation Studies of Methane Oxidative Coupling on a $Na/NiTiO_3$ Catalyst," *Ind. Eng. Chem. Res.*, 30, 1157–1165, (1991) to be favorable for MOC.

What is claimed is:

1. A method for oxidative coupling of methane comprising the steps of:

contacting a gaseous mixture of methane and oxygen with a methane oxidative coupling catalyst, said methane oxidative coupling catalyst comprising $Fe_2O_3$ deposited on a silica substrate, said silica substrate having a geometric surface area of about 0.04 $m^2/g$.

2. A method in accordance with claim 1, wherein said methane oxidative coupling catalyst is disposed within a fluidized bed reactor.

3. A method in accordance with claim 1, wherein said methane oxidative coupling catalyst further comprises a plurality of water molecules on said silica substrate.

4. A method in accordance with claim 1, wherein said silica substrate has particle sizes in the range of about 150 to 215 μm.

5. A method in accordance with claim 1, wherein said silica substrate is essentially non-porous.

6. A method in accordance with claim 1, wherein said methane oxidative coupling catalyst is essentially non-porous and a surface concentration of iron is on the order of about 2% by weight of said catalyst.

7. A method in accordance with claim 1, wherein said gaseous mixture further comprises steam.

* * * * *